United States Patent [19]
Shuto et al.

[11] Patent Number: 4,573,193
[45] Date of Patent: Feb. 25, 1986

[54] INDIVIDUAL IDENTIFICATION APPARATUS

[75] Inventors: Yukichi Shuto, Abiko; Tamotsu Miyagawa, Inazawa, both of Japan

[73] Assignee: Mitsubishi Denki Kabushiki Kaisha, Tokyo, Japan

[21] Appl. No.: 627,605

[22] Filed: Jul. 3, 1984

[30] Foreign Application Priority Data

Jul. 25, 1983 [JP] Japan ................................. 58-135612

[51] Int. Cl.$^4$ .............................................. G06K 9/00
[52] U.S. Cl. .......................................... 382/2; 382/4; 340/825.34
[58] Field of Search ................... 382/2, 4; 340/825.31, 340/825.34

[56] References Cited

U.S. PATENT DOCUMENTS

| 3,576,537 | 4/1971 | Ernst | 382/2 |
| 3,576,538 | 4/1971 | Miller | 382/2 |
| 3,648,240 | 3/1972 | Jacoby et al. | 382/2 |
| 4,206,441 | 6/1980 | Kondo | 382/2 |

OTHER PUBLICATIONS

"Primary aberrations of Fresnel lenses" by Erwin Delano, *Journal of the Optical Society of America*, vol. 64, No. 4.

*Primary Examiner*—Leo H. Boudreau
*Assistant Examiner*—Jacqueline Todd
*Attorney, Agent, or Firm*—Oblon, Fisher, Spivak, McClelland & Maier

[57] ABSTRACT

Four fingers of a hand of an individual person, i.e. the index finger, the middle finger, the medical finger and the little finger are placed on a transparent measuring table in juxtaposition. A guide member is also placed on the table to restrict the position of the hand and light is irradiated onto the table. The intensity of the light passed through the transparent measuring table is scanned by a television camera and so on at every light receiving point to convert it an electrical signal. Thus obtained electric signals are processed to calculate the differential data of the finger lengths thereby detecting an individual person.

10 Claims, 6 Drawing Figures

INDIVIDUAL IDENTIFICATION APPARATUS

This invention relates to an apparatus for identifying an individual person by measuring a shape of a hand of the individual with a required precision and by using combination of such measured data.

FIG. 1 of the accompanying drawing illustrates a conventional individual identification apparatus, in which a reference numeral 1 designates a plane projection of a hand on a measuring table, and numerals 1001 to 1006 refer to sensors for measuring lengths of fingers placed on the measuring table. These sensors are line sensors of a type which detects an end point s of each finger on the measuring table covering the sensor. In more detail, when the hand is placed on the measuring table at a position as indicated by a solid line, the detection points of the individual sensors are designated by $S1a$ to $S6a$. In contrast to this, when the same hand is placed on the measuring table at a position as indicated by a broken line, which is slightly deviated from that shown by the solid line, the detection points of the individual sensors are designated by $S1b$ to $S6b$, which are of course different from the detection points $S1a$ to $S6a$. This results in differentiated values of the finger length data for one and the same hand owing to very small difference in the position of the hand placed on the measuring table. In more detail, when the finger length data for the index finger, the middle finger, the medical finger, and the little finger of the hand placed at the solid line position are set to be $l_1$, $l_2$, $l_3$ and $l_4$, respectively, the finger length data for the respective fingers of the hand placed at the broken line position are denoted as follows: $l_1-(S3a-S3b)-(S1b-S1a)$ for the index finger; $l_2-(S4a-S4b)-(S1b-S1a)$ for the middle finger; $l_3-(S5a-S5b)-(S2b-S2a)$ for the medical finger; and $l_4-(S6a-S6b)-(S2b-S2b)$ for the little finger.

That is to say, it will be seen that, in the conventional device, when the placing position of the hand varies in the measurement of the finger length, not only variations in the finger tip portion but also variations in the web portion would remarkably affect the finger length data. As the consequence of this, there have been various disadvantages with the conventional individual identification apparatus such that, at the time of measuring the finger length, the tip end as well as the web of the fingers should be accurately matched with the sensors, which would require considerable amount of attention to be paid on the manner of placing the hand on the surface of the measuring table, or, in the event of inaccurate positioning of the hand, the identifying operation needs to be done repeatedly, and so forth.

The present invention has been made with a view to removing the above-mentioned various disadvantages inherent in the conventional device.

It is therefore an object of the present invention to provide an individual identification apparatus capable of carrying out the identification of an individual person with high precision and accuracy.

It is another object of the present invention to provide an individual identification apparatus with minimum necessity for repeating the identifying operation of an individual person.

It is still another object of the present invention to provide an individual identification apparatus free from stringent requirement imposed on the placing position of the hand on the measuring table at the identifying operation.

It is other object of the present invention to provide an individual identification apparatus which can be made small in size.

In order to attain the above-mentioned objects, the present invention has made it possible to detect differential data of the finger lengths in a manner not to be affected by variations in the webs of the hand.

According to the present invention in general aspect of it, there is provided an individual identification apparatus, which comprises: a transparent measuring table, on which four fingers of a hand of an individual to be an object of identification, i.e., the index finger, the middle finger, the medical finger, and the little finger, are placed in juxtaposition; a guide member mounted on said measuring table to restrict the position of the hand on it; a light source for irradiating light onto said measuring table; a two-dimensional photo-electric conversion device to receive light irradiated from said light source and passed through said measuring table, and to generate electrical signals of an intensity to be determined by an intensity of the light at every light receiving point on the two-dimensional plane; means for outputting electrical signals generated at every light receiving point of said two-dimensional photo-electric conversion device as the video electrical signals by scanning said two-dimensional plane at a predetermined scanning speed; a comparator for quantizing intensity of the video electrical signal from said output means into a level of intensity of the transmitting light at the portion where the hand and the guide member are not placed on said measuring table and a level of intensity of the transmitting light at the portion where both are placed; and an information processing unit which detects size information of a hand on said measuring table by the output from said comparator and said scanning speed, and takes three differential data of the finger lengths between the mutually adjacent fingers of the four fingers of the hand, i.e., the index finger, the middle finger, the medical finger and the little finger, from said detected information as the factors for identifying an individual as the object of the identification.

The foregoing objects, other objects as well as specific construction and function of the individual indentification apparatus according to the present invention will become more apparent and understandable from the following detailed description thereof, when read in conjunction with the accompanying drawing.

In the following, the present invention will be described in detail with reference to the particular embodiments thereof shown in the accompanying drawing.

Figure 1:
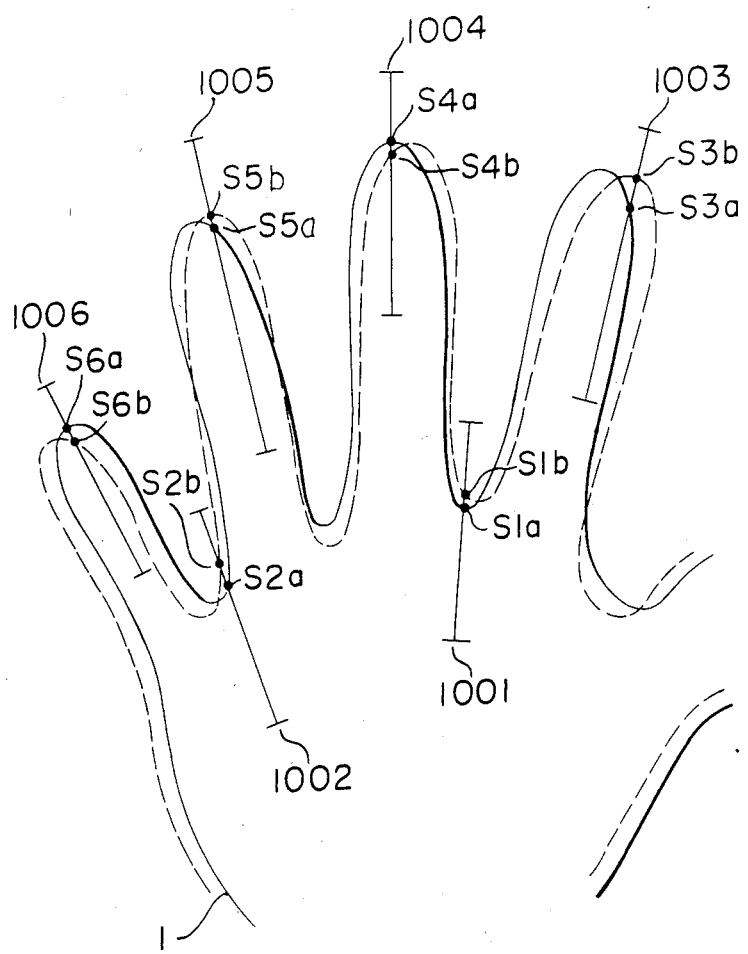
FIG. 1 is an explanatory diagram showing a conventional individual identification apparatus.
Figure 2:
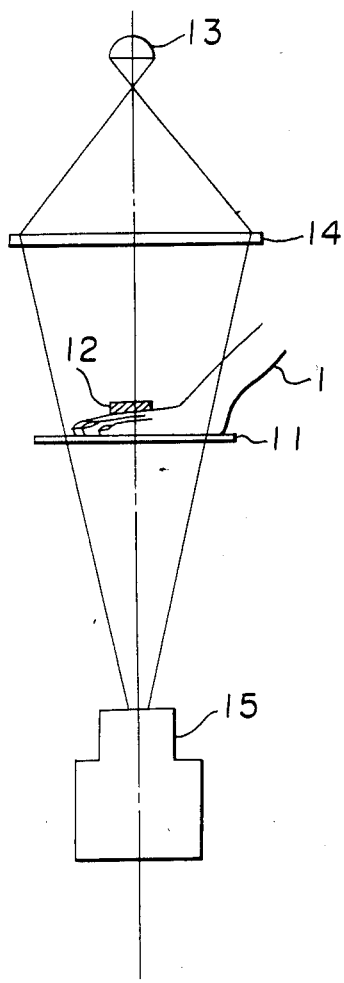
FIG. 2 is a schematic diagram showing one preferred embodiment of the individual identification apparatus according to the present invention.

Referring first to FIG. 2 showing a schematic diagram of the individual identification apparatus according to one preferred embodiment of the present invention, a reference numeral 1 denotes a hand of an individual person to be an object of identification, which corresponds to the hand 1 shown in FIG. 1; a numeral 11 refers to a transparent measuring table, on which to place the hand 1; a reference numeral 12 denotes a guide member for accurate positioning of the hand 1 on the measuring table 11; a numeral 13 refers to a light source such as a halogen lamp and so forth; a numeral 14 refers to Fresnel lens which functions to collimate light from the light source into the parallel beam of light, and to irradiate the same onto the measuring table 11; and a reference numeral 15 designates a two-dimensional photo-electric conversion device such as, for example, a television camera or a two-dimensional solid-state camera, and others, which receives light which has passed through the measuring table 11.

Figure 3:
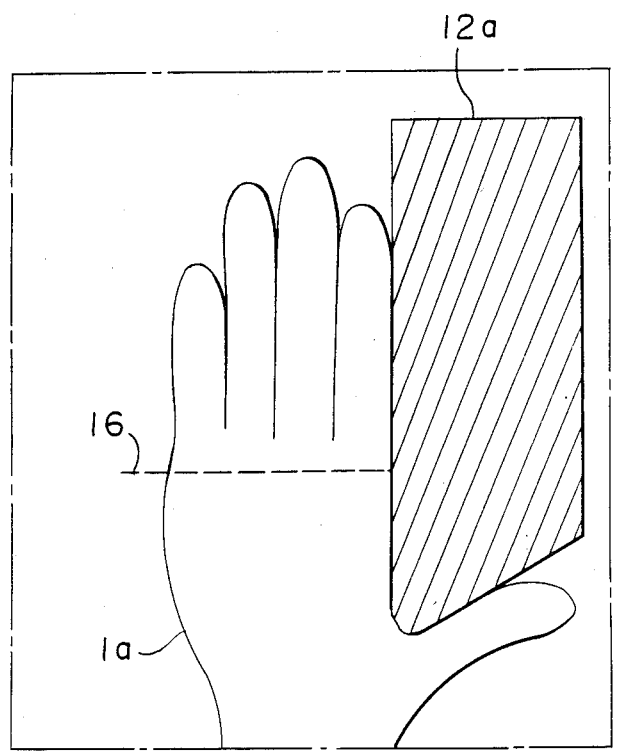
FIG. 3 is an explanatory diagram showing an image focussed on an image forming screen of a two-dimensional photo-electric converter in FIG. 2.

FIG. 3 is an explanatory diagram showing an image focussed on an image forming screen of the two-dimensional photo-electric conversion device 15, wherein a reference numeral 1a designates an image of the hand 1, a numeral 12a refers to an image of the guide member 12, and a reference numeral 16 denotes a virtual base line to be a reference at the time of measuring the finger length.

Figure 4:
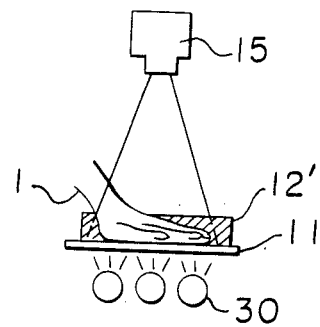
FIG. 4 is a schematic diagram showing another embodiment of the individual identification apparatus according to the present invention.

FIG. 4 is a schematic diagram illustrating another embodiment of the individual identification apparatus according to the present invention, wherein those parts which are identical with, or corresponding to, those in FIG. 2 are designated by the same reference numerals. In FIG. 4, a numeral 30 refers to a plurality of fluorescent lamps, which correspond to the light source 13 in FIG. 2. Also, a reference numeral 12' designates the guide member for accurate positioning of the hand 1 on the measuring table 11. This guide member 12' is disposed in such a manner that the little finger of the hand 1 may be in contact with it. Further, in the embodiment shown in FIG. 2, light is irradiated from the light source 13 situated above the hand 1. In contrast to this, according to the embodiment shown in FIG. 4, light is irradiated onto the hand 1 from the light source positioned below the hand 1 through the measuring table 11.

Figure 5:
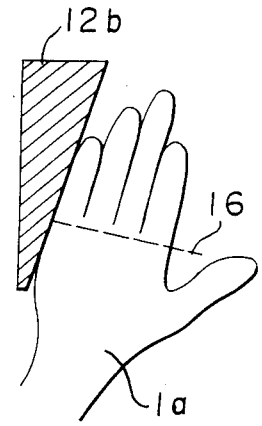
FIG. 5 is an explanatory diagram showing an image focussed on the image forming screen of the two-dimensional photo-electric converter shown in FIG. 4.

FIG. 5 is an explanatory diagram showing an image focussed on the image forming screen of the two-dimensional photo-electric conversion device 15 in FIG. 4. In the drawing, a reference numeral 1a denotes an image of the hand 1, a numeral 12b refers to an image of the guide member 12', and a reference numeral 16 designates a virtual base line to be a reference at the time of measuring the finger length.

It should be noted that the embodiment shown in FIG. 4 makes it unnecessary to use the Fresnel lens, unlike the embodiment shown in FIG. 2, so that the device as a whole can be made small in size.

Figure 6:
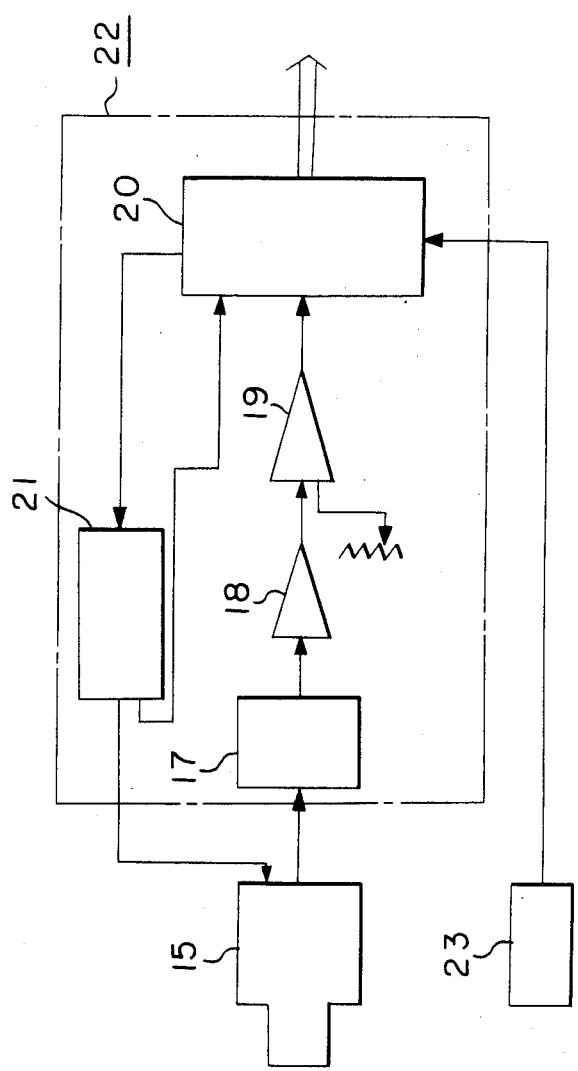
FIG. 6 is a block diagram showing a processing unit for processing signals in the embodimental devices shown in FIGS. 2 and 4.

FIG. 6 is a block diagram showing a processing unit for processing output signals from the two-dimensional photo-electric conversion device 15. In the drawing, a numeral 15 refers to the same two-dimensional photo-electric conversion device as shown in FIG. 2. For the sake of convenience in the ensuing explanation of the embodiment shown in FIG. 2 using this circuit block diagram, this photo-electric conversion device is specified as a television camera. A numeral 17 refers to a receiving circuit, a numeral 18 refers to an amplifier, a reference numeral 19 denotes a comparator, a reference numeral 20 indicates a controller, a dot-and-dash line designated by a reference numeral 22 and containing therein the receiving circuit 17, the amplifier 18, the comparator 19, the controller 20, and a timing signal generator 21 denotes a signal processing unit, and a numeral 23 refers to a switch for generating a signal to start the operations in the signal processing unit 22.

When the hand 1 is positioned on the measuring table 11 and the switch 23 is operated, the signal processing unit 22 is actuated with the signal, whereby the timing signal generator 21 generates a sweep signal for carrying out both horizontal and vertical scanning of the television camera 15, and sends out to the controller 20 the horizontal synchronous signal and the vertical synchronous signal, both of which creates the basic point for the sweeping operation. It should be understood that, for the convenience of the data processing in the controller 20, the television camera 15 and the measuring table 11 are so registered that both the horizontal scanning direction and the vertical scanning direction of the television camera 15 may be made coincident in the directions of the two sides of the image of the guide member 12a which are at the right angle each other.

At every light receiving point of the television camera 15, there is generated an electric quantity having an intensity corresponding to the intensity of the light which the light receiving point has received. Video signals which have sequentially scanned the electric quantities are output from the television camera 15. These output video signals are converted to quantized (two-value) signals (i.e., the signals having a high level and a low level only) by the signal receiving circuit 17, the amplifier 18, and the comparator 19. A reference voltage in the comparator 19 is so set that, as shown in FIG. 3, the portions 1a and 12a may assume the low level, and the remaining portions may assume the high level.

The controller 20 is able to calculate the differential data of the finger lengths by first introducing thereinto the quantized signals from the comparator 19 and the horizontal and vertical synchronous signals from the timing signal generator 21, and then processing these input signals as introduced. For instance, if the virtual base line 16 is set as a line to be coincident with the horizontal scanning line after lapse of a predetermined time from the vertical synchronous signal of the television camera 15, it is easy to determine the length from the virtual base line 16 to the tip end of each finger by detection of the horizontal scanning line where the low level signal becomes extinct in correspondence to each finger through the controller 20. The differential data of the finger lengths can be calculated as $H_2-H_1$, $H_2-H_3$, and $H_2-H_4$, provided that these numerical values for the data are $H_1$ for the index finger, $H_2$ for the middle finger, $H_3$ for the medical finger, and $H_4$ for the little finger.

The foregoing explanations have been made in reference to the circuit block diagram of FIG. 6 in conjunction with the embodiment shown in FIG. 2, and the same operations can be effected with the embodiment shown in FIG. 4.

According to the individual identification apparatus of the present invention, since the finger length measurement is effected by use of the two-dimensional photo-electric conversion device and with the virtual base line as the reference, there is no possibility of the position of the horizontal scanning line including the image at the distal end of the finger being affected to a substantial extent, even when there is a slight deviation in the finger position, and of errors being produced depending on the position of the web, as has been experienced in the conventional line sensors.

Incidentally, according to this two-dimensional photo-electric conversion device, it is also easy to detect size information of a width of the palm, and such size information can also be added to the individual identifying information.

Also, in the foregoing explanations of FIG. 6, the two-dimensional photo-electric conversion device 15 has been explained as the television camera. It should however be noted that a two-dimensional solid-state camera or a conversion device of a type, in which a single-dimensional individual camera is moved by a mechanical expedient in the two-dimensional direction, may be used as the two-dimensional photo-electric conversion device 15. Further, it is feasible to design the device such that, instead of receiving the transmitting light by the television camera, reflecting light may be received by it.

As has been stated in the foregoing, the present invention possesses the remarkably advantageous effect such that the individual identification can be done with high precision without imposing any stringent requirement on the manner of positioning the hand on the measuring table, and with the least necessity for repeating the identification work due to mal-positioning of the hand.

Although the present invention has been described with reference to particular embodiments thereof, it will be understood that the invention is not limited by this embodiment alone, but any changes and modifications may be made by those persons skilled in the art within the spirit and scope of the invention as set forth in the appended claims.

We claim:

1. An individual identification apparatus, which comprises:
   (a) a transparent measuring table, on which four fingers of a hand of an individual person to be an object of identification are placed in juxtaposition;
   (b) a guide member mounted on said measuring table to restrict the position of the hand on it and establish finger lengths;
   (c) a light source for irradiating light onto said measuring table;
   (d) a two-dimensional photo-electric conversion device to receive light irradiated from said light source and passed through said measuring table, and to generate electrical signals of an intensity to be determined by an intensity of the light at every light receiving point on the two-dimensional plane;
   (e) means for outputting electrical signals generated at every light receiving point of said two-dimensional photoelectric conversion device as the video electrical signals by scanning said two-dimensional plane at a predetermined scanning speed;
   (f) a comparator for quantizing intensity of the video electrical signal from said output means into a level of intensity of the transmitting light at the portion where the hand and the guide member are not placed on said measuring table and a level of intensity of the transmitting light at the portion where both are placed; and
   (g) an information processing unit for receiving said quantized intensity of the video electric signal from said comparator for establishing a base line perpendicular to said guide member on said hand, and for determining therefrom the distance between said base line and the tips of said four fingers and the three differences between the distances of adjacent fingers and for identifying an individual person as the object of the identification on the basis of said three differences.

2. The individual identification apparatus according to claim 1, in which said light source is a halogen lamp.

3. The individual identification apparatus according to claim 2, in which light from said halogen lamp is irradiated onto the measuring table through a Fresnel lens.

4. The individual identification apparatus according to claim 3, in which said halogen lamp is disposed on the same side of said measuring table as said hand.

5. The individual identification apparatus according to claim 1, in which said light source is a plurality of fluorescent lamps.

6. The individual identification apparatus according to claim 5, in which light from said plurality of fluorescent lamps is irraidated onto the hand through said measuring table.

7. The individual identification apparatus according to claim 1, in which said guide member to be provided on said measuring table is positioned between the thumb and the index finger of the hand to be placed on said measuring table.

8. The individual identification apparatus according to claim 1, in which said guide member to be provided on said measuring table is positioned next to the little finger of a hand to be placed on said measuring table.

9. The individual identification apparatus according to claim 1, wherein said two-dimensional photo-electric conversion device is a television camera.

10. The individual identification apparatus according to claim 1, in which said two-dimensional photo-electric conversion device is a two-dimensional solid-state camera.

* * * * *